(12) United States Patent
Ishiyama

(10) Patent No.: US 11,427,733 B2
(45) Date of Patent: Aug. 30, 2022

(54) TAPE SET

(71) Applicant: Kobayashi Pharmaceutical Co., Ltd., Osaka (JP)

(72) Inventor: Ryutaro Ishiyama, Ibaraki (JP)

(73) Assignee: Kobayashi Pharmaceutical Co., Ltd., Osaka (JP)

(*) Notice: Subject to any disclaimer, the term of this patent is extended or adjusted under 35 U.S.C. 154(b) by 56 days.

(21) Appl. No.: 16/960,363

(22) PCT Filed: Jan. 7, 2019

(86) PCT No.: PCT/JP2019/000074
§ 371 (c)(1),
(2) Date: Jul. 7, 2020

(87) PCT Pub. No.: WO2019/138963
PCT Pub. Date: Jul. 18, 2019

(65) Prior Publication Data
US 2020/0369922 A1  Nov. 26, 2020

(30) Foreign Application Priority Data
Jan. 9, 2018  (JP) .............................. JP2018-001493

(51) Int. Cl.
*C09J 7/26* (2018.01)
*C09J 7/21* (2018.01)

(52) U.S. Cl.
CPC .  *C09J 7/26* (2018.01); *C09J 7/21* (2018.01); *Y10T 428/192* (2015.01)

(58) Field of Classification Search
CPC ............ C09J 7/26; C09J 7/21; Y10T 428/192
See application file for complete search history.

(56) References Cited

U.S. PATENT DOCUMENTS

2008/0286533 A1  11/2008  Gotz et al.
2009/0294030 A1  12/2009  Nagel et al.

FOREIGN PATENT DOCUMENTS

CN  204490789 U  7/2015
CN  206521419 U  9/2017
(Continued)

OTHER PUBLICATIONS

[NPL-1] Tadashi Sano (JP S51-020065 U), Feb. 14, 1976 (EPO machine translation). (Year: 1976).*
(Continued)

*Primary Examiner* — Frank J Vineis
*Assistant Examiner* — Donald M Flores, Jr.
(74) *Attorney, Agent, or Firm* — Locke Lord LLP; James E. Armstrong, IV; Nicholas J. DiCeglie, Jr.

(57) ABSTRACT

This invention provides a tape set capable of increasing the portion (share) for tape pieces in a base paper in the shaping of tape pieces. A tape set 1 includes at least one tape T1 and at least one tape T2, each extending in the longitudinal direction. The tape T1 and tape T2 each include a wavy part W having one or more basic components K, both side edges of which having an outward-facing convex shape from a first bottom point P to a second bottom point P via a vertex Q. The tape T1 and tape T2 are arranged in a width direction orthogonal to the longitudinal direction so that the wavy parts W of the tape T1 and tape T2 are adjoined to each other. The tape T1 further includes a section T1-1 that continues from an edge of the wavy part W on one end side.

20 Claims, 12 Drawing Sheets

(56) References Cited

FOREIGN PATENT DOCUMENTS

| | | | |
|---|---|---|---|
| JP | 1976-20065 U | | 2/1976 |
| JP | 51020065 U | * | 2/1976 |
| JP | 2002-336286 A | | 11/2002 |
| JP | 2009-512770 A | | 3/2009 |
| JP | 2009-293028 A | | 12/2009 |
| JP | 2011-033822 A | | 2/2011 |
| JP | 2011-174957 A | | 9/2011 |
| JP | 2012-093643 A | | 5/2012 |

OTHER PUBLICATIONS

International Search Report dated Apr. 16, 2019, issued for PCT/JP2019/000074.
Office Action issued in corresponding Chinese Patent Application No. CN 201980007762.5, dated Nov. 12, 2021.

* cited by examiner

TAPE SET

TECHNICAL FIELD

The present invention relates to a tape set including multiple tape pieces.

BACKGROUND ART

Conventionally, tape sets including multiple tape pieces adhering to a release film have been used. For example, Patent Literature (PTL) 1 discloses a tape set in which product information is printed on each tape piece. In the tape set of PTL 1, each tape piece has a rectangular shape.

Examples of the tape set include a tape set for suppressing mouth breathing during sleep. FIG. 11 shows a conventional tape 10 for suppressing mouth breathing. The tape 10 for suppressing mouth breathing includes multiple pieces of tape T made of non-woven fabric or the like adhering to a release film F. The tape T is peeled off from the release film F and is adhered to the lips, whereby mouth breathing during sleep can be suppressed. In the tape 10 for suppressing mouth breathing, both of the side edges of each piece of tape T have a wavy shape so that the tape T is easily stretched and does not easily come off from the lips. In this example shown in the figure, the wavy shape at the side edges of the tape T is composed of a series of four basic wavy edges C. Each basic wavy edge C has an outward-curved convex shape from a first bottom point p to a second bottom point p via a vertex Q. Each piece of tape T has the same distance $L_N$ between one end in the longitudinal direction and a vertex $Q_N$ of the Nth wavy shape counted from one end side in the longitudinal direction. (FIG. 11 shows, as an example, the distance $L_2$ between one end in the longitudinal direction and a vertex $Q_2$ of the second wavy shape counted from the one end side in the longitudinal direction, and the distance $L_4$ between one end in the longitudinal direction and a vertex $Q_4$ of the fourth wavy shape counted from the one end side in the longitudinal direction).

CITATION LIST

Patent Literature

PTL 1: JP2011-33822A

SUMMARY OF INVENTION

Technical Problem

In the production of a tape set, multiple tape pieces can be shaped to be arranged in a line by die-cutting a base paper adhering to a release film. When doing so, increasing the share (portion used for tape pieces) in the base paper is required to reduce the cost of materials. In this regard, tape pieces having a rectangular shape as disclosed in PTL 1 can be produced, for example, by preparing a base paper having a width equal to the tape length to thus increase the share in the base paper, and die-cutting the base paper along straight driving lines at multiple positions spaced by the width of the tape. In this manner, the tape pieces can be shaped so that each tape piece extends over the entire width of the base paper (each tape piece has a length equal to the width of the base paper), and so that the short sides of two adjacent tape pieces are adjoined to each other.

On the other hand, in a conventional tape set (the tape 10 for suppressing mouth breathing), each piece of tape T has the same distance $L_N$ between one end in the longitudinal direction and the Nth vertex $Q_N$. Therefore, as shown in FIG. 12, in order to die-cut a base paper G so that each piece of tape T extends substantially over the entire width of the base paper G in the longitudinal direction, the Nth vertex $Q_N$ of each piece of tape T must be located along the same straight line in the width direction (the longitudinal direction here refers to the longitudinal direction of each piece of tape T, and the width direction refers to the direction orthogonal to the longitudinal direction of each piece of tape T). Therefore, the side edges of two adjacent pieces of tape T, T cannot be adjoined to each other, and a gap V (a portion V that is not used for pieces of tape T in the base paper G) is formed between the two pieces of tape T, T. This reduces the share for the tape pieces in the base paper G.

The present invention has been made to solve the above problems. An object of the present invention is to provide a tape set capable of increasing the portion (share) for tape pieces in a base paper in the shaping of tape pieces.

Solution to Problem

To solve the problems described above, the present invention provides the following tape set.

A tape set including at least one first tape and at least one second tape, each extending in the longitudinal direction, wherein the first tape and the second tape each include a wavy part having one or more basic components, both side edges of each of the one or more basic components having an outward-facing convex shape from a first bottom point to a second bottom point via a vertex, the first tape and the second tape are arranged in a width direction orthogonal to the longitudinal direction so that the wavy part of the first tape and the wavy part of the second tape are adjoined to each other, the first tape further includes a section 1-1 that continues from an edge of the wavy part on one end side and whose tip edge is located along the same straight line as an edge of the wavy part of the second tape on the one end side extending in the width direction, and the second tape further includes a section 2-1 that continues from an edge of the wavy part on the other end side and whose tip edge is located along the same straight line as an edge of the wavy part of the first tape on the other end side extending in the width direction.

It is preferable that a side edge of the section 1-1 on the second tape side is adjoined to an inclined part constituting the side edge of the basic component of the second tape from a vertex to a bottom point on the one end side, while a side edge of the section 2-1 on the first tape side is adjoined to an inclined part constituting the side edge of the basic component of the first tape from a vertex to a bottom point on the other end side.

It is preferable that the section 1-1 and the section 2-1 have the same shape.

It is preferable that the section 1-1 and the section 2-1 each have side edges extending outward.

It is preferable that when a one-end-side-bottom-point line extending in the width direction through bottom points on the one end side, a vertex line extending in the width direction through vertexes, and an other-end-side-bottom-point line extending in the width direction through bottom points on the other end side are used as boundaries to divide the basic component into a one-end-side area between the one-end-side-bottom-point line and the vertex line, and an other-end-side area between the vertex line and the otherend-side-bottom-point line, the section 1-1 and the other-end-side area in the basic component of the first tape have the same shape, and the section 2-1 and the one-end-side area in the basic component of the second tape have the same shape.

It is preferable that the first tape further includes a section 1-2 that continues from the tip edge of the section 1-1, and a section 1-3 that continues from the edge of the wavy part on the other end side, the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction, and the section 1-2, the section 1-3, the section 2-2, and the section 2-3 each have side edges extending inward.

It is preferable that the section 1-2 and the section 2-2 have the same shape, and the section 1-3 and the section 2-3 have the same shape.

It is preferable that the side edges of the section 1-2 smoothly continue from the side edges of the section 1-1, the side edges of the section 2-2 smoothly continue from the side edges of the section 2-1, the side edges of the section 1-3 smoothly continue from the side edges of the other-end-side area of the basic component of the first tape, and the side edges of the section 2-3 smoothly continue from the side edges of the one-end-side area of the basic component of the second tape.

It is preferable that the first tape further includes a section 1-2 that continues from the tip edge of the section 1-1, and a section 1-3 that continues from the edge of the wavy part on the other end side, the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction, the section 1-2 and the section 2-2 each have side edges extending inward, the section 1-3 and the section 2-3 each have side edges extending outward, the side edges of the section 1-2 and the section 2-3 are adjoined to each other, and the side edges of the section 1-3 and the section 2-2 are adjoined to each other.

It is preferable that the section 1-2 and the section 2-2 have the same shape, and the section 1-3 and the section 2-3 have the same shape.

It is preferable that the side edges of the section 1-2 have the same gradient as that of the side edges of the one-end-side area of the basic component of the first tape, the side edges of the section 1-3 have the same gradient as that of the side edges of the one-end-side area of the basic component of the first tape, the side edges of the section 2-2 have the same gradient as that of the side edges of the other-end-side area of the basic component of the second tape, and the side edges of the section 2-3 have the same gradient as that of the side edges of the other-end-side area of the basic component of the second tape.

Advantageous Effects of Invention

The tape set of the present invention is capable of increasing the portion (share) for tape pieces in a base paper in the shaping of tape pieces.

DESCRIPTION OF EMBODIMENTS

Figure 1:
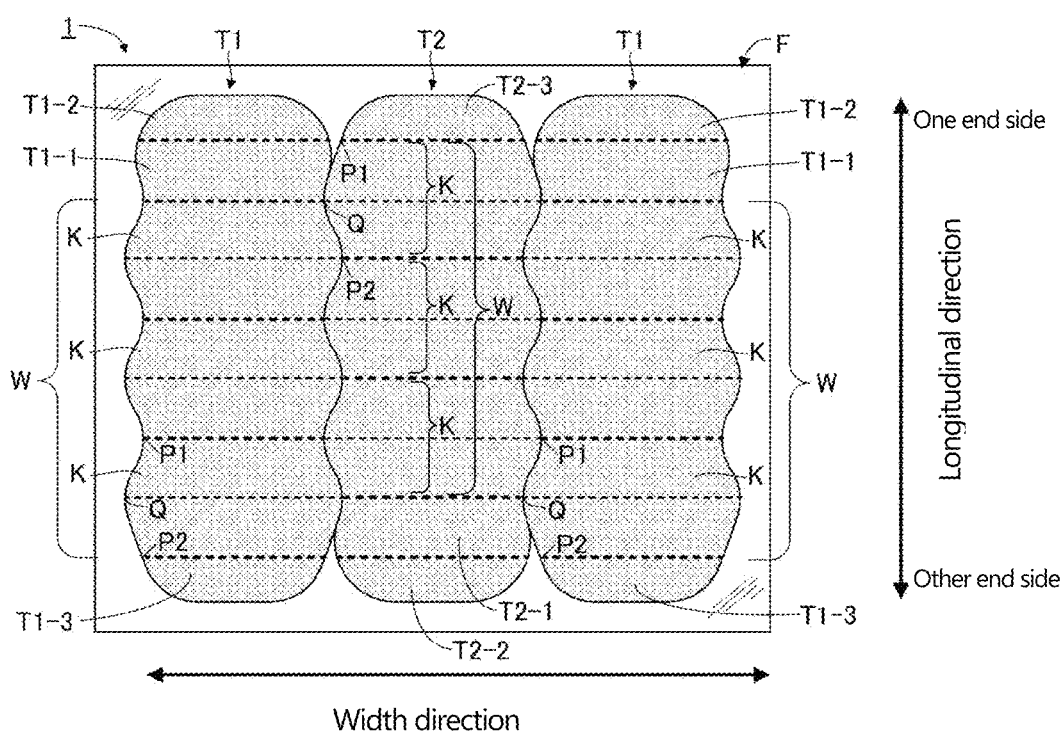
FIG. 1 is a plan view showing a tape set according to an embodiment of the present invention.

Embodiments of the present invention are described below with reference to the drawings. FIG. 1 is a plan view showing a tape set 1 according to an embodiment of the present invention.

The tape set 1 of FIG. 1 includes a piece of tape T1 and a piece of tape T2 extending in the longitudinal direction and adhering to a release film F. The tape set 1 is used by peeling the tape T1 and tape T2 off from the release film F and adhering them to the lips, whereby mouth breathing during sleep can be suppressed.

The release film F is made of plastic or paper. The release film F has a rectangular shape, and the tape T1 and tape T2 extend over substantially the entire width of the release film F in the longitudinal direction.

The tape T1 and tape T2 are made of, for example, non-woven fabric, Japanese paper, or a resin sheet with multiple air holes. An adhesive that has been applied to the back surface of the tape T1 and tape T2 allows the tape T1 and tape T2 to be adhered to the release film F or the lips. The adhesive may be, for example, a silicon-based adhesive, a urethane-based adhesive, or an acrylic-based adhesive. To use the tape for suppressing mouth breathing, a silicone-based adhesive is preferable from the viewpoint of skin irritation etc.

To allow the tape T1 and tape T2 to be easily stretched, and to not easily come off from the lips, the tape T1 and the tape T2 each include a wavy part W. The wavy part W has one or more (three in the illustrated example) basic components K, and the side edges of each basic component K have an outward-facing curved convex shape from a first bottom point P to a second bottom point P via a vertex Q. The expression "outward" means that both side edges extend to gradually increase the length of the tape T in the width direction. The tape T1 and tape T2 are arranged in the width direction orthogonal to the longitudinal direction so that the wavy part W of the tape T1 and the wavy part W of the tape T2 are adjoined to each other. FIG. 1 shows an example in which two pieces of tape T1 and one piece of tape T2 are adhered to a release film F so that the pieces of tape T1 are adjoined to both sides of the tape T2. However, the tape set 1 may include one or more combinations of the tape T1 and tape T2 as long as the tape T1 and tape T2 can be adhered to the release film F in a state in which they are arranged alternately.

Figure 2:
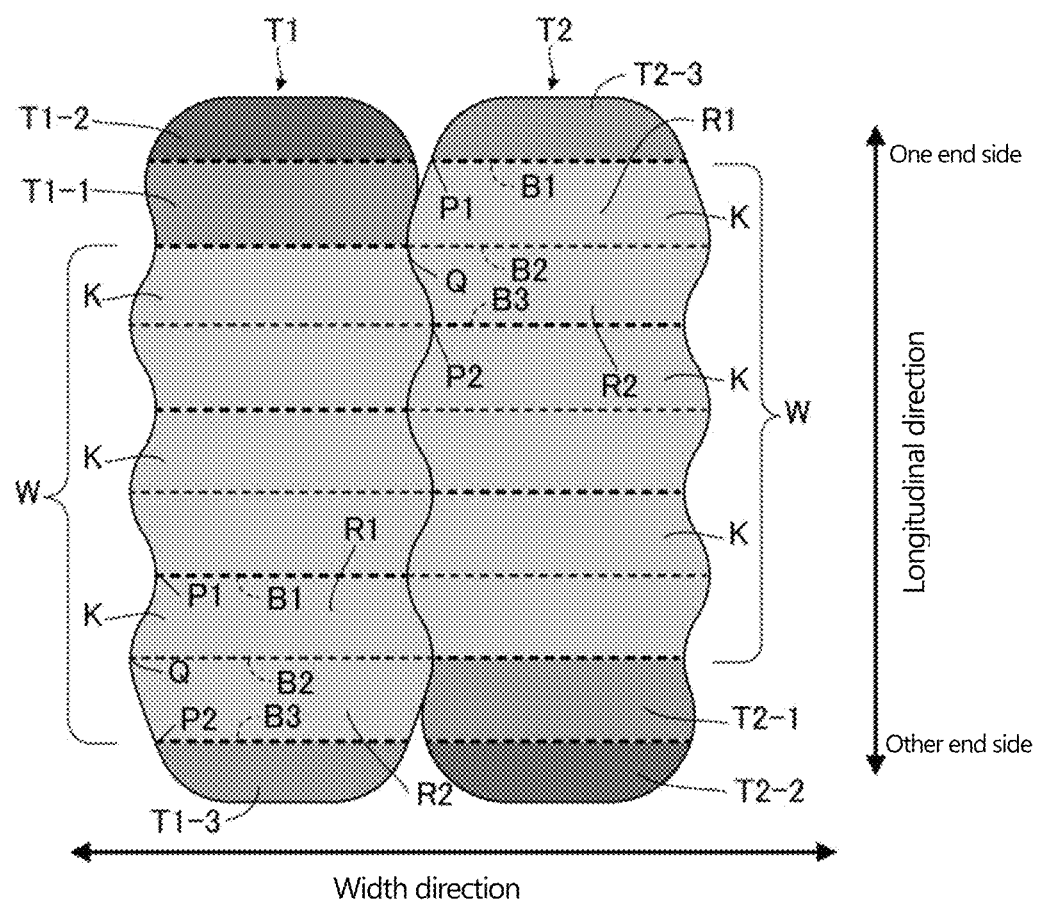
FIG. 2 is a plan view showing tape pieces of the tape set of FIG. 1.

FIG. 2 is a plan view showing only adjacent tape T1 and tape T2. (In FIG. 2, for convenience of explanation, the portions with the same shape in each tape piece are shown in the same colors.) The straight line B1 shown in FIG. 2 is an imaginary line extending in the width direction through bottom points P1 at one end side (referred to below as "the one-end-side-bottom-point line B1"). The straight line B2 shown in FIG. 2 is an imaginary line extending in the width direction through vertexes Q (referred to below as "the vertex line B2"). The straight line B3 shown in FIG. 2 is an imaginary line extending in the width direction through bottom points P2 on the other end side (referred to below as "the other-end-side-bottom-point line B3"). "R1" in FIG. 2 represents a one-end-side area between the one-end-side-bottom-point line B1 and the vertex line B2 in a basic component K. "R2" in FIG. 2 represents an other-end-side area between the vertex line B2 and the other-end-side-bottom-point line B3 in a basic component K. When the side edges of the wavy parts W of the tape T1 and tape T2 are adjoined to each other, the vertexes Q of one of the tape pieces match the bottom points P of the other tape, while the bottom points P of one of the tape pieces match the vertexes Q of the other tape. Therefore, the wavy parts W of the tape T1 and tape T2 shift from each other in the longitudinal direction. That is, in the tape T1, the other-end-side area R2 of the wavy part W projects beyond the edge of the wavy part W of the tape T2 on the other end side, and in the tape T2, the one-end-side area R1 of the wavy part W projects beyond the edge of the wavy part W of the tape T1 on the one end side.

The tape T1 includes a section T1-1 at a location at a side of the projecting one-end-side area R1 of the tape T2. The tape T2 includes a section T2-1 at a location at a side of the projecting other-end-side area R2 of the tape T1. The section T1-1 and the section T2-1 are described below.

The section T1-1 continues from the edge of the wavy part W of the tape T1 on the one end side. In the section T1-1, both side edges extend outward, and the tip edge of the section T1-1 on the one end side and the edge of the wavy part W of the tape T2 on the one end side are located along the same straight line extending in the width direction.

The section T1-1 has the same shape as the other-end-side area R2 of the basic component K of the tape T1, and the side edge of the section T1-1 on the tape T2 side is adjoined to an inclined part of the tape T2 constituting the side edge of the basic component K from the vertex Q to the bottom point P1 on the one end side.

In the present invention, the expression "the same shape" indicates that two parts in the tape T1 and tape T2 satisfy the following conditions (1) to (3).
(1) The length in the longitudinal direction is the same.
(2) The end edge in the longitudinal direction has the same width.
(3) The side edges both extend either inward or outward from the end edge in the longitudinal direction having the same width.

When two parts in the tape T1 and tape T2 have the same shape, it includes a case in which the two parts have exactly the same shape, a case in which the two parts have a point-symmetric shape, and a case in which the two parts have the same gradient at one side edge but have different gradients at the other side edge.

The section T2-1 continues from the edge of the wavy part W of the tape T2 on the other end side. In the section T2-1, both side edges extend outward, and the tip edge of the section T2-1 on the other end side and the edge of the wavy part W of the tape T1 on the other end side are located along the same straight line extending in the width direction.

The section T2-1 has the same shape as the one-end-side area R1 of the basic component K of the tape T2. Therefore, the side edge of the section T2-1 on the tape T1 side is adjoined to an inclined part of the tape T1 constituting the side edge of the basic component K from the vertex Q to the bottom point P2 on the other end side, and the section T1-1 and the section T2-1 have the same shape.

In addition to the wavy part W and the section T1-1, the tape T1 further includes a section T1-2 that continues from the tip edge of the section T1-1 on the one end side, and a section T1-3 that continues from the edge of the wavy part W on the other end side. In addition to the wavy part W and the section T2-1, the tape T2 further includes a section T2-2 that continues from the tip edge of the section T2-1 on the other end side, and a section T2-3 that continues from the edge of the wavy part W on the one end side.

The side edges of the section T1-2, the section T1-3, the section T2-2, and the section T2-3 extend inward to be connected to each other consecutively. The expression "inward" means that both side edges extend to gradually decrease the length of the tape T in the width direction.

The tip edge of the section T1-2 on the one end side and the tip edge of the section T2-3 on the one end side are located along the same straight line extending in the width direction. The tip edge of the section T1-3 on the other end side and the tip edge of the section T2-2 on the other end side are located along the same straight line extending in the width direction. To allow the tape T1 and the tape T2 to have exactly the same shape, the section T1-2 and the section T2-2 have the same shape, while the section T1-3 and the section T2-3 have the same shape.

It is preferable that the side edges of the section T1-2 smoothly continue to the side edges of the section T1-1, and that the side edges of the section T2-2 smoothly continue to the side edges of the section T2-1. Thus, the side edges of the section T1-2 and the section T2-2 constitute wavy side edges that continue to the side edges of the section T1-1 or the section T2-1.

It is also preferable that the side edges of the section T1-3 smoothly continue to the side edges of the other-end-side area R2 of the tape T1, and that the side edges of the section T2-3 smoothly continue to the side edges of the one-end-side area R1 of the tape T2. Thus, the side edges of the section T1-3 and the section T2-3 constitute wavy side edges that continue to the side edges of the respective wavy parts W.

The tape set 1 described above is produced by sequentially performing the following steps 1 to 3:
Step 1: preparing a base paper G adhering to a release film F;
Step 2: die-cutting the base paper G with a punch E; and
Step 3: removing a portion that is not used for pieces of the tape T from the base paper G.

Figure 3:
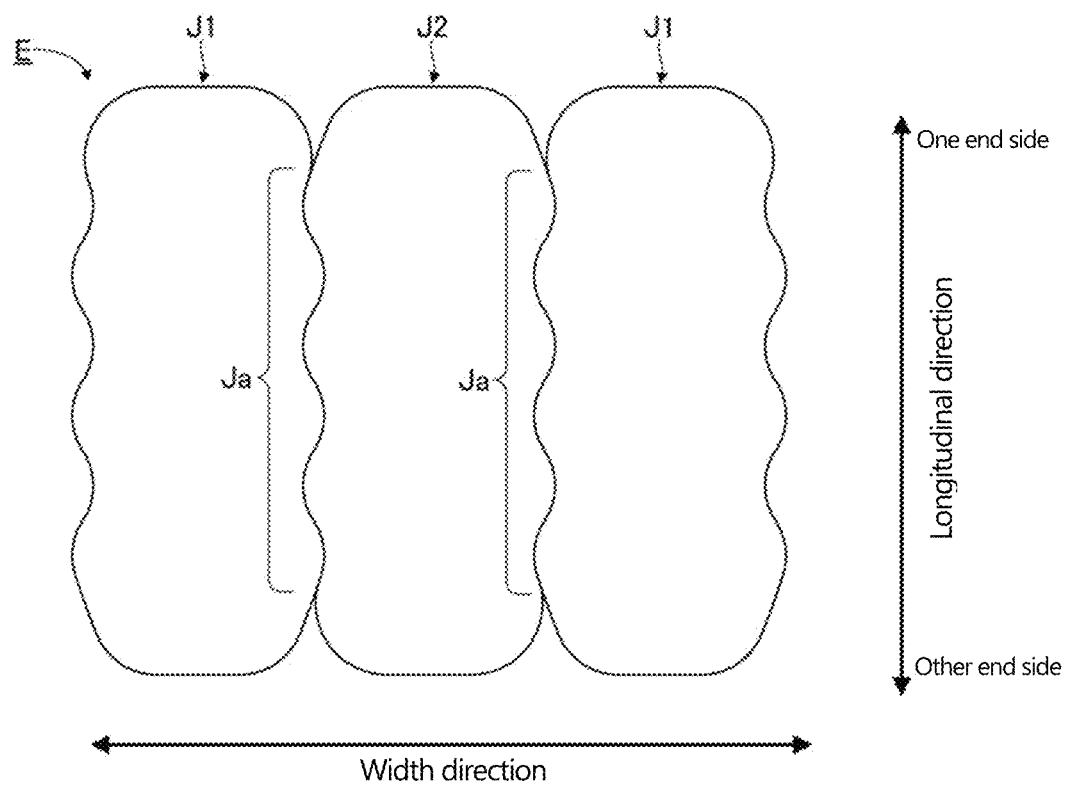
FIG. 3 is a plan view showing a punch for die-cutting a base paper for tape pieces.
Figure 4:
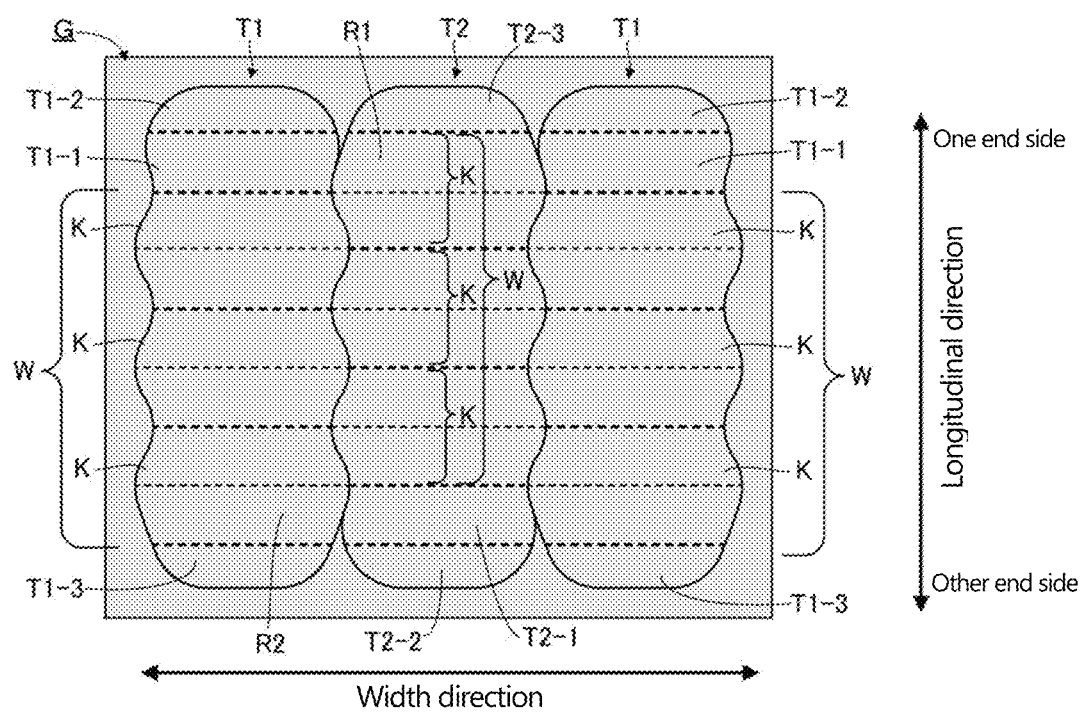
FIG. 4 is a plan view showing the state of the base paper immediately after being die-cut with the punch.

FIG. 3 is a plan view showing a punch E used to die-cut a base paper G for pieces of the tape T. FIG. 4 is a plan view showing the base paper G after being die-cut with the punch E.

In the punch E shown in FIG. 3, an annular body J1 for shaping a piece of tape T1 (referred to below as "the first annular body J1") and an annular body J2 for shaping a piece of tape T2 ("second annular body J2") are alternately arranged. The adjacent first annular body J1 and the second annular body J2 are consecutively connected via a wavy wall Ja (i.e., the adjacent first annular body J1 and the second annular body J2 share the wavy wall Ja as a part thereof). The wavy walls Ja are provided to shape wavy side edges of the tape T1 and tape T2. The adjacent first annular body J1 and the second annular body J2 shape the tape T1 and tape T2 whose wavy side edges are adjoined to each other (see FIG. 4). The expression "wavy side edges" here includes the side edges of the wavy parts W of the tape T1 and tape T2, the side edges of the other-end-side area R2 of the tape T1, the side edges of the section T1-1, the side edges of the one-end-side area R1 of the tape T2, and the side edges of the section T2-1.

According to the tape set 1 of this embodiment, the tape T1 and tape T2 are arranged in the width direction so that the side edge of the wavy part W of the tape T1 and the side edge of the wavy part W of the T2 are adjoined to each other. Thus, the tape T1 and tape T2 can be shaped without forming a gap between the wavy parts W of the tape T1 and tape T2 (a portion that is not used for pieces of the tape T in the base paper G).

Further, the side edge of the section T1-1 of the tape T1 is adjoined to the side edge of the one-end-side area R1 constituting the wavy part W of the tape T2 on the one end side, while the side edge of the section T2-1 of the tape T2 is adjoined to the side edge of the other-end-side area R2 constituting the wavy part W of the tape T1 on the other end side. Accordingly, the tape T1 and tape T2 can be shaped without forming a gap (a portion that is not used for pieces of the tape T in the base paper G) not only at the area in which the wavy parts W are adjoined to each other, but also at the side areas of the wavy parts W on the one end side and the other end side.

Additionally, the tip edge of the section T1-2 on the one end side and the tip edge of the section T2-3 on the one end side are located along the same straight line extending in the width direction, while the tip edge of the section T1-3 on the other end side and the tip edge of the section T2-2 on the other end side are located along the same straight line extending in the width direction. Therefore, the tape T1 and tape T2 can be shaped using a base paper G with a length corresponding to the length of the tape T1 and tape T2 in the longitudinal direction.

For the above reasons, the tape set 1 according to this embodiment is capable of increasing the share in the base paper G (capable of reducing the portion that is discarded without being used for tape pieces in the base paper G).

In the tape T1 and tape T2, the side edges of the sections T1-1, T1-2, T1-3, T2-1, T2-2, and T2-3 also constitute the wavy side edges, together with the side edges of the wavy parts W. Therefore, all of the side edges of the tape T1 and tape T2 have a wavy shape. It is thus possible to improve the performance of the tape T1 and tape T2; i.e., the tape is more easily stretched and less easily comes off from the lips (referred to below as "the performance of the tape T1 and tape T2, such as stretchability").

In this embodiment, the wavy parts W of the tape T1 and the tape T2 have the same shape, the section T1-1 and the section T2-1 have the same shape, the section T1-2 and the section T2-2 have the same shape, and the section T1-3 and the section T2-3 have the same shape. Therefore, the tape T1 and the tape T2 have the exact same shape, achieving uniform performance of the tape T1 and tape T2, such as stretchability.

Both of the side edges of the sections T1-2, T1-3, T2-2, and T2-3 extend inward. Therefore, the corners of the wavy parts W and the sections that constitute the base end of these sections do not easily turn over (for example, since both side edges of the section T1-2 extend inward, the corners of the section T1-1 that constitute the base end of the section T1-2 do not easily turn over). Therefore, the tape T1 and tape T2 are stably maintained in a state in which the tape T1 and tape T2 are adhered to the release film F or the lips.

The present invention is not limited to the embodiment described above and can be variously modified.

Figure 5:
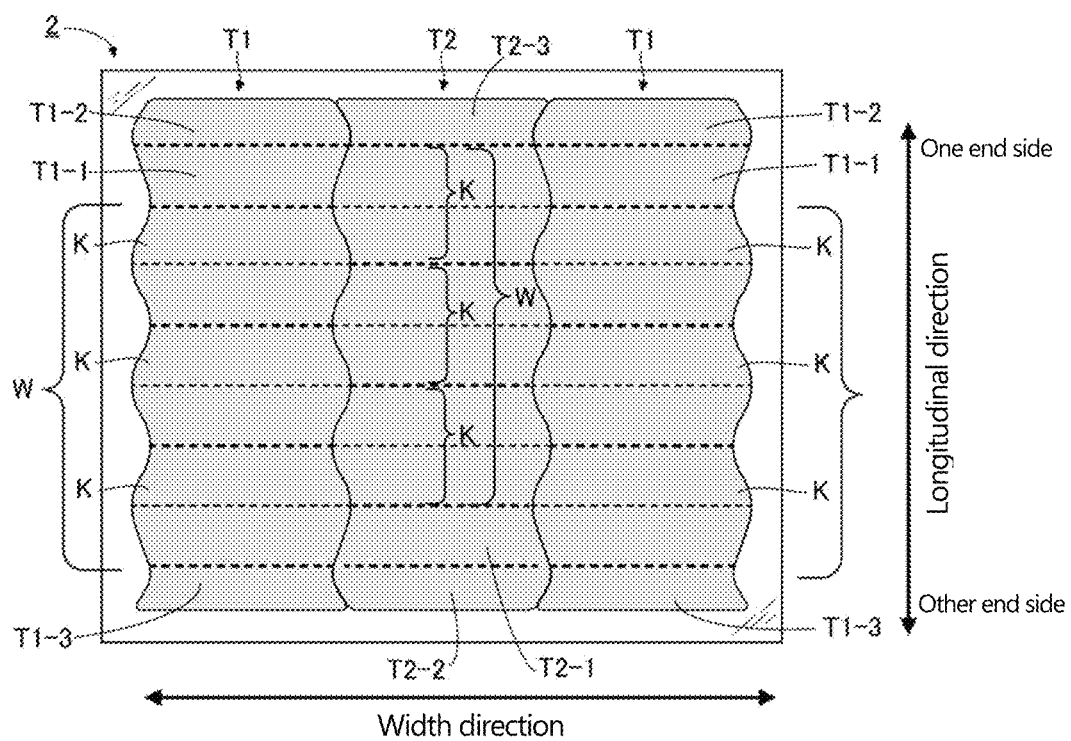
FIG. 5 is a plan view showing a tape set according to a modification example of the present invention.
Figure 6:
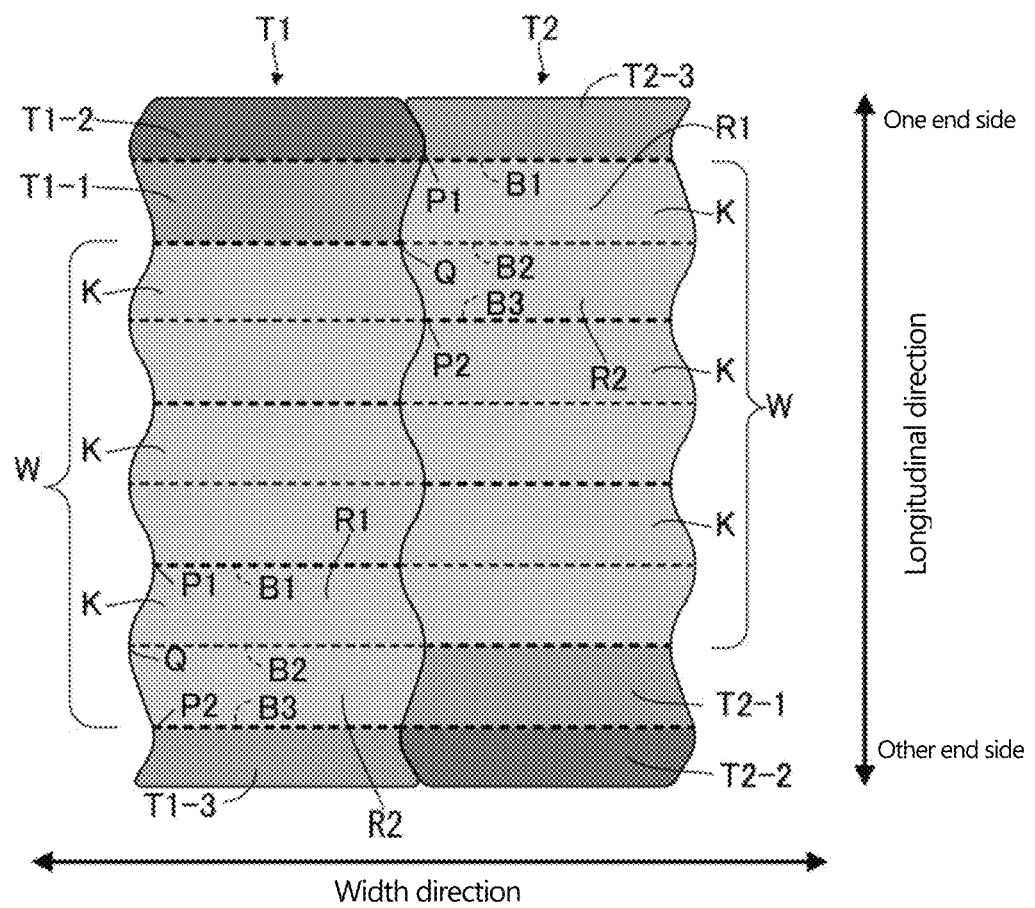
FIG. 6 is a plan view showing the tape pieces of the tape set of FIG. 5.

For example, the tape set of the present invention can be modified as shown in FIG. 5. FIG. 5 is a plan view showing a tape set 2 according to a modification example of the present invention. FIG. 6 is a plan view showing the tape T1 and tape T2 of the tape set 2 of FIG. 5. (In FIG. 6, for convenience of explanation, the portions with the same shape in each tape piece are shown in the same color.)

The tape set 2 shown in FIG. 5 is the same as the tape set 1 shown in FIG. 1 except that the shape of the section T1-3 and the shape of the section T2-3 are changed. In this tape set 2, the section T1-3 and the section T2-3 have the same shape, with both of their side edges extending outward. The tip edge of the section T1-3 on the other end side and the tip edge of the section T2-2 on the other end side are located along the same straight line extending in the width direction. The tip edge of the section T2-3 on the one end side and the tip edge of the section T1-2 on the one end side are located along the same straight line extending in the width direction.

The tape set 2 exhibits the same effects as the embodiment described above. Additionally, the tape set 2, in which the side edges of the section T1-3 and the section T2-3 extend outward, can reduce the gap between the section T1-2 and the section T2-3 and the gap between the section T1-3 and the section T2-2 (portions that are not used for tape pieces in the base paper G). This can further increase the share in the base paper G.

It is preferable that the side edges of the section T1-3 have the same gradient as that of the side edges of the one-end-side area R1 of the tape T1, and that the side edges of the section T2-2 have the same gradient as that of the side edges of the other-end-side area R2 of the tape T2. Further, the side edges of the section T1-2 have the same gradient as that of the side edges of the one-end-side area R1 of the tape T1, and the side edges of the section T2-3 have the same gradient as that of the side edges of the other-end-side area R2 of the tape T2. In this manner, the side edge of the section T1-3 and the side edge of the section T2-2 can be adjoined to each other, and the side edge of the section T1-2 and the side edge of section T2-3 can be adjoined to each other. This can further increase the share in the base paper G.

Figure 7:
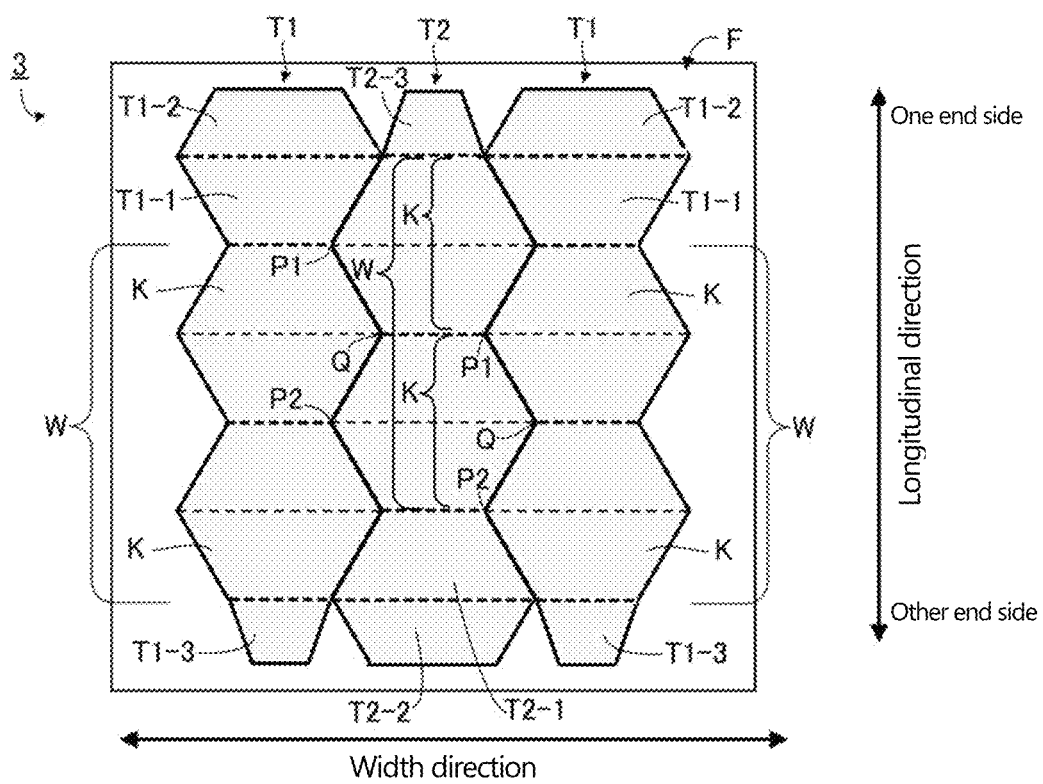
FIG. 7 is a plan view showing a tape set according to a modification example of the present invention.
Figure 8:
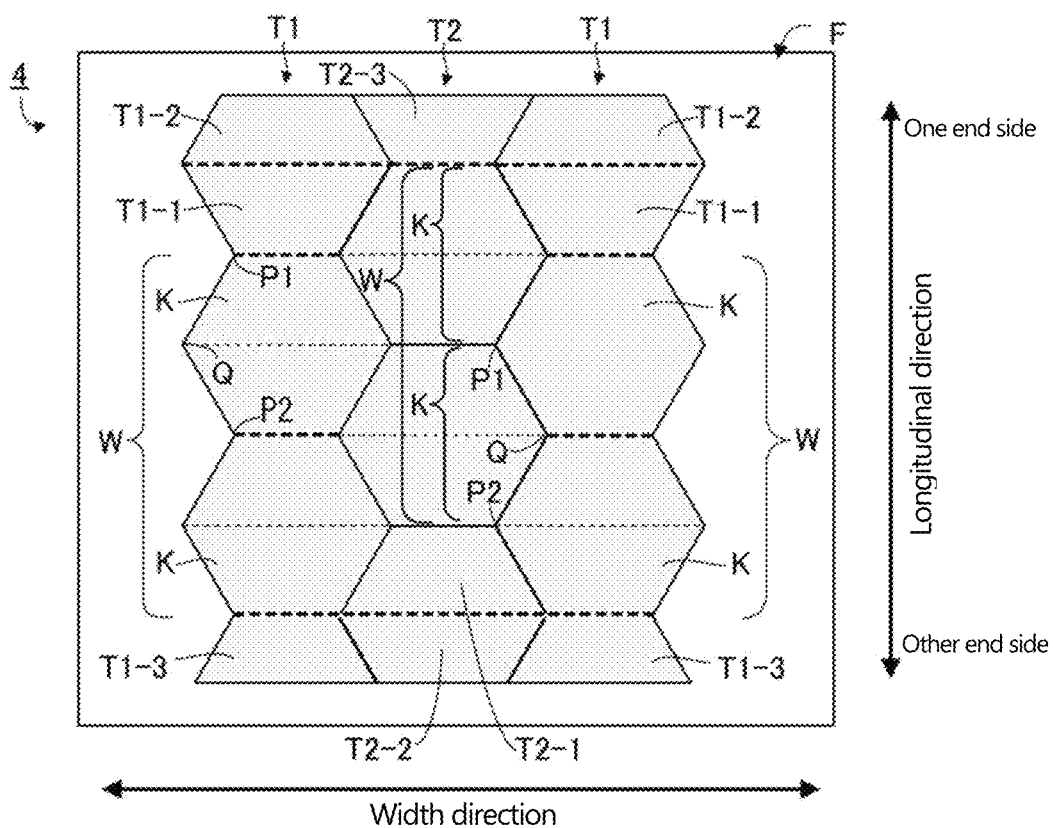
FIG. 8 is a plan view showing a tape set according to a modification example of the present invention.

The side edges of the basic components K are not limited to have the curved convex shape shown in the above embodiment, and they may have a triangular projection shape as shown in FIGS. 7 and 8.

The tape set 3 shown in FIG. 7 is a modification example of the tape set 1 shown in FIG. 1. The tape set 4 shown in FIG. 8 is a modification example of the tape set 2 shown in FIG. 5. The tape sets 1 shown in FIG. 7 and FIG. 8 each have two basic components K, and the side edges of the basic components K have outward-facing triangular projection shapes.

In the tape sets 3 an 4 of FIG. 7 and FIG. 8, the side edges of the section T1-1 have the same gradient as that of the inclined parts constituting the side edges of the basic component K of the tape T1 from the vertex Q to the bottom point P2 on the other end side to allow the section T1-1 to be adjoined to the wavy part W of the tape T2. Further, the side edges of the section T2-1 have the same gradient as that of the inclined parts constituting the side edges of the basic components K of the tape T2 from the vertex Q to the bottom point P1 on the one end side to allow the section T2-1 to be adjoined to the wavy part W of the tape T1.

In the tape set 3 shown in FIG. 7, in order to increase the length of the wavy side edges of the tape T1, the side edges of the section T1-2 have the same gradient as that of the inclined parts constituting the side edges of the basic component K of the tape T1 from the vertex Q to the bottom point P1 on the one end side. Also, in order to increase the length of the wavy side edges of the tape T2, the side edges of the section T2-2 have the same gradient as that of the inclined parts constituting the side edges of the basic component K of the tape T2 from the vertex Q to the bottom point P2 on the other end side.

In the tape set 4 shown in FIG. 8, in order to increase the length of the wavy side edges of the tape T1, the side edges of the section T1-2 and the section T1-3 each have the same gradient as that of the inclined parts constituting the side edges of the basic component K of the tape T1 from the vertex Q to the bottom point P1 on the one end side. Also, in order to increase the length of the wavy side edges of the tape T2, the side edges of the section T2-2 and the section T2-3 each have the same gradient as that of the inclined parts constituting the side edges of the basic component K of the tape T2 from the vertex Q to the bottom point P2 on the other end side. Since the gradients of the side edges of the sections T1-2, T1-3, T2-2, and T2-3 are adjusted as described above, the side edge of the section T1-2 is adjoined to the side edge of the section T2-3, while the side edge of the section T1-3 is adjoined to the side edge of the section T2-2.

A tape set 3 shown in FIG. 7 exhibits the same effects as those of the tape set 1 shown in the above embodiment (FIG. 1), and a tape set 4 shown in FIG. 8 exhibits the same effects as those of the tape set 2 of FIG. 5.

Figure 9:
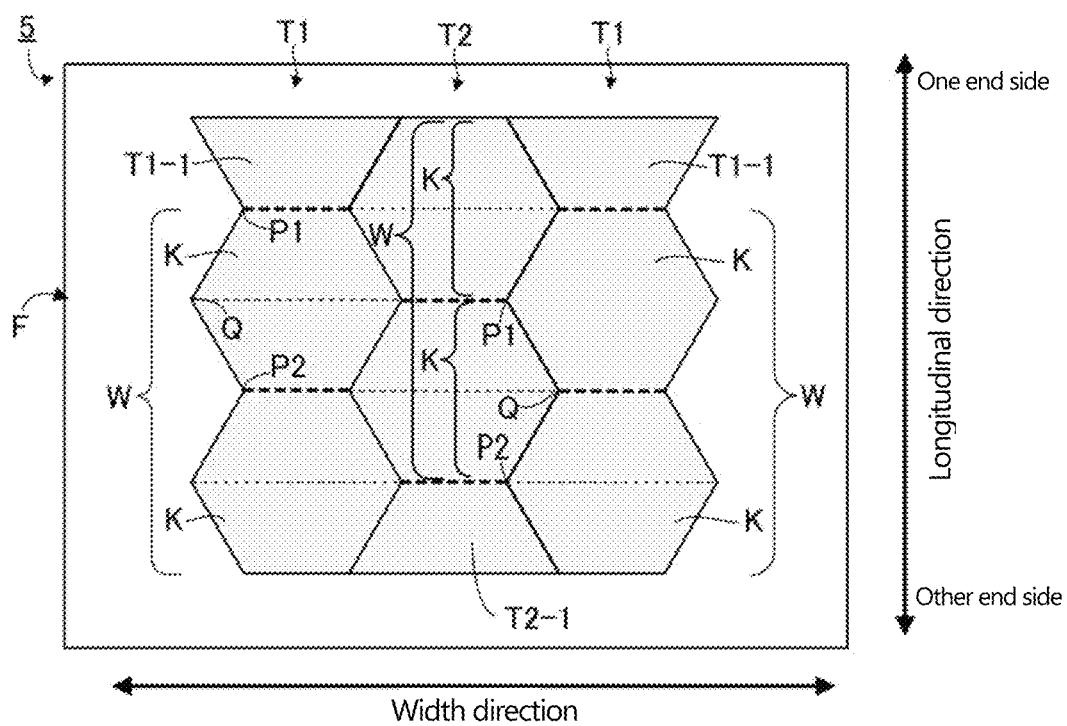
FIG. 9 is a plan view showing a tape set according to a modification example of the present invention.

The tape sets 3 and 4 of FIG. 7 and FIG. 8 can be further modified as shown in FIG. 9. Tape set 5 shown in FIG. 9 is the same as the tape sets 3 and 4 of FIGS. 7 and 8 except that the sections T1-2, T1-3, T2-2, and T2-3 are omitted.

In the tape set 5 shown in FIG. 9, as in the embodiments described above, the wavy part W of the tape T1 and the wavy part W of the tape T2 are adjoined to each other, the side edge of the section T1-1 of the tape T1 is adjoined to the side edge of the wavy part W of the tape T2 on the one end side, while the side edge of the section T2-1 of the tape T2 is adjoined to the side edge of the wavy part W of the tape T1 on the other end side. The tip edge of the section T1-1 on the one end side and the edge of the wavy part W of the tape T2 on the one end side are located along the same straight line extending in the width direction, while the tip edge of the section T2-1 on the other end side and the edge of the wavy part W of the tape T1 on the other end side are located along the same straight line extending in the width direction. Therefore, the tape T1 and tape T2 can be shaped using a base paper G with a length corresponding to the length of the tape T1 and tape T2 in the longitudinal direction. This can increase the share in the base paper G.

Figure 10:
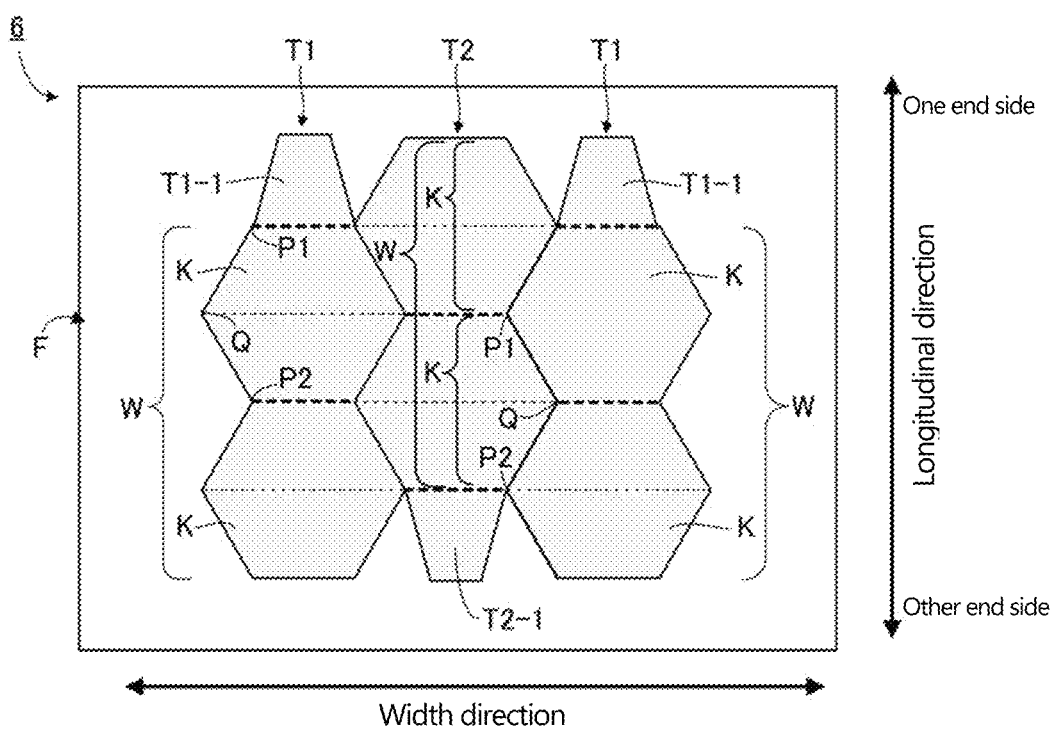
FIG. 10 is a plan view showing a tape set according to a modification example of the present invention.
Figure 11:
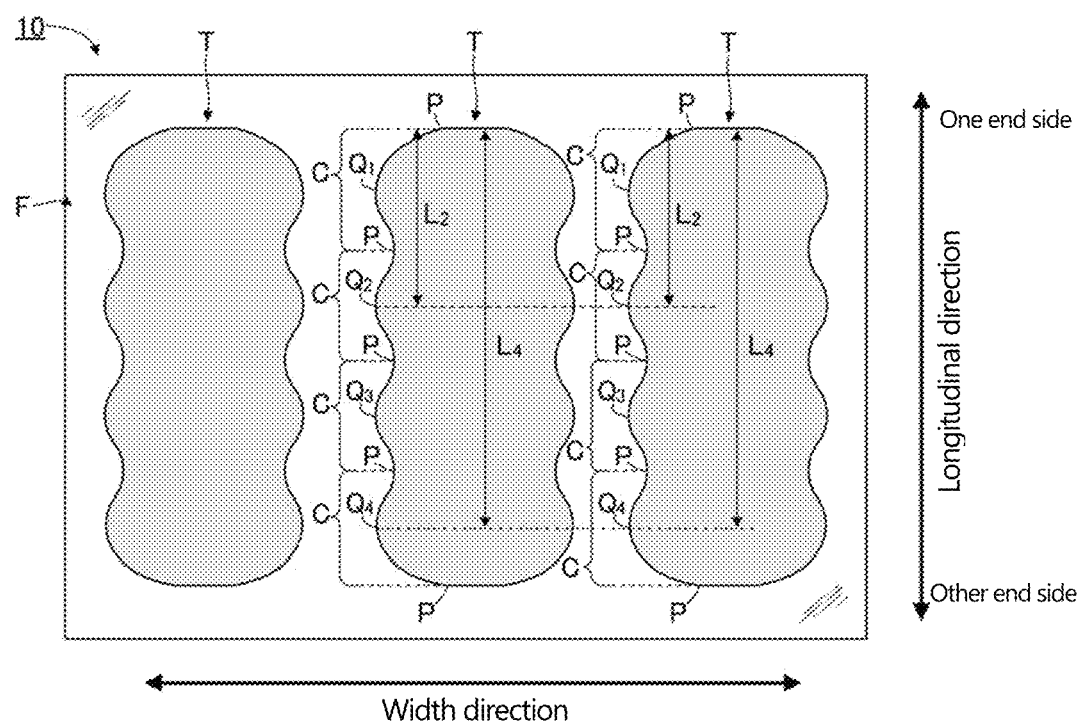
FIG. 11 is a plan view showing a conventional tape set.
Figure 12:
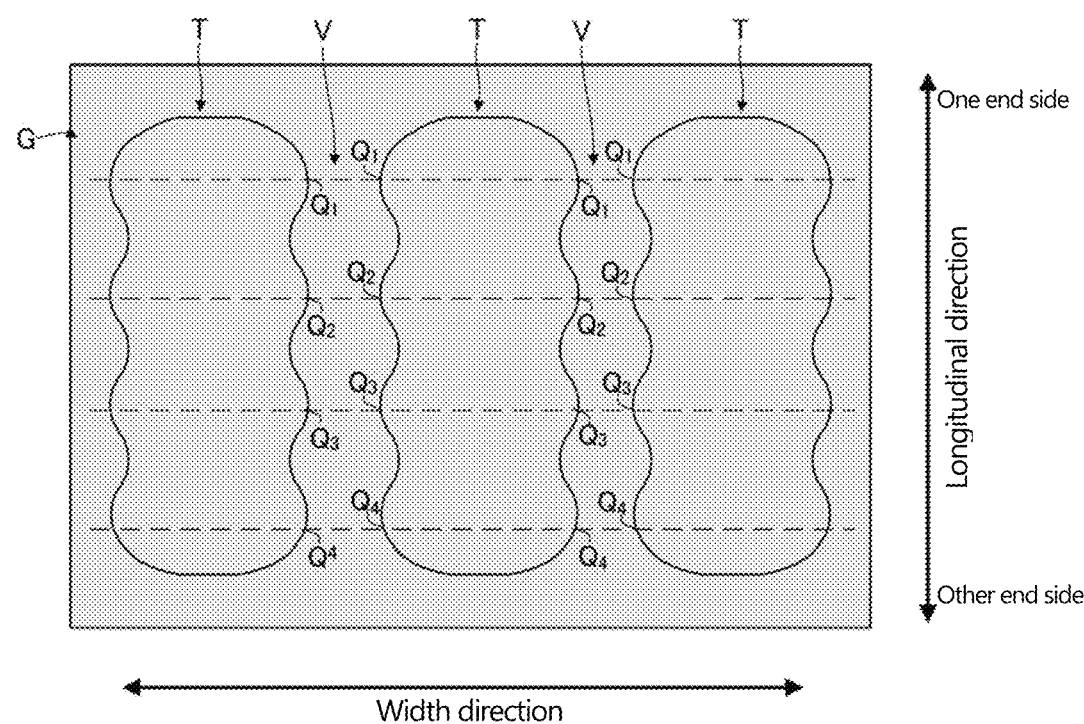
FIG. 12 is a plan view showing the state of a base paper that has been die-cut to a shape of a conventional tape set.

The tape set 5 shown in FIG. 9 can be further modified as shown in FIG. 10. The tape set 6 of FIG. 10 is the same as the tape set 5 of FIG. 9 except that the side edge of the section T1-1 is not adjoined to the side edge of the wavy part W of the tape T2 on the one end side, and the side edge of the section T2-1 is not adjoined to the side edge of the wavy part W of the tape T1 on the other end side.

In the tape set 6 of FIG. 10, as in the embodiments described above, the tape T1 and tape T2 are arranged in the width direction so that the wavy part W of the tape T1 and the wavy part W of the tape T2 are adjoined to each other. Furthermore, as in the tape set 5 of FIG. 9, the tip edge of the section T1-1 on the one end side and the edge of the wavy part W of the tape T2 on the one end side are located along the same straight line extending in the width direction, while the tip edge of the section T2-1 on the other end side and the edge of the wavy part W of the tape T1 on the other end side are located along the same straight line extending in the width direction. Therefore, the tape T1 and tape T2 can be shaped using a base paper G with a length corresponding to the length of the tape T1 and tape T2 in the longitudinal direction. This can increase the share in the base paper G.

In the tape sets 1, 2, 3, 4, 5, and 6 shown in FIGS. 1 and 5 to 8, the section T1-1 and the section T2-1 do not necessarily have the same shape, the section T1-2 and the section T2-2 do not necessarily have the same shape, and the section T1-3 and the section T2-3 do not necessarily have the same shape.

In the examples described above, the tape sets according to the present invention are applied to tape pieces for suppressing mouth breathing; however, the tape sets according to the present invention are applicable to a variety of products in which two or more tape pieces with wavy side edges are arranged.

DESCRIPTION OF THE REFERENCE NUMERALS 1, 2, 3, 4, 5, 6. Tape set
B1. One-end-side-bottom-point line
B2. Vertex line
B3. Other-end-side-bottom-point line
F. Release film
K. Basic component
P1. Bottom point on the one end side
P2. Bottom point on the other end side
Q. Vertex
R1. One-end-side area
R2. Other-end-side area
T1. Tape (first tape)
T2. Tape (second tape)
T1-1. Section (section 1-1)
T1-2. Section (section 1-2)
T1-3. Section (section 1-3)
T2-1. Section (section 2-1)
T2-2. Section (section 2-2)
T2-3. Section (section 2-3)
W. Wavy part

The invention claimed is:

1. A tape set including at least one first tape and at least one second tape, each extending in the longitudinal direction,
wherein
the first tape and the second tape each include a wavy part having one or more basic components, both side edges of each of the one or more basic components having an outward-facing convex shape from a first bottom point to a second bottom point via a vertex,
the first tape and the second tape are arranged in a width direction orthogonal to the longitudinal direction so that the wavy part of the first tape and the wavy part of the second tape are adjoined to each other,
the first tape further includes a section 1-1 that continues from an edge of the wavy part on one end side and whose tip edge is located along the same straight line as an edge of the wavy part of the second tape on the one end side extending in the width direction,
the second tape further includes a section 2-1 that continues from an edge of the wavy part on the other end side and whose tip edge is located along the same straight line as an edge of the wavy part of the first tape on the other end side extending in the width direction, and
wherein the tape set adheres to a release film.

2. The tape set according to claim 1, wherein a side edge of the section 1-1 on the second tape side is adjoined to an inclined part constituting the side edge of the basic component of the second tape from a vertex to a bottom point on the one end side, while a side edge of the section 2-1 on the first tape side is adjoined to an inclined part constituting the side edge of the basic component of the first tape from a vertex to a bottom point on the other end side.

3. The tape set according to claim 1, wherein the section 1-1 and the section 2-1 have the same shape.

4. The tape set according to claim 3, wherein the section 1-1 and the section 2-1 each have side edges extending outward.

5. The tape set according to claim 4, wherein when a one-end-side-bottom-point line extending in the width direction through bottom points on the one end side, a vertex line extending in the width direction through vertexes, and an other-end-side-bottom-point line extending in the width direction through bottom points on the other end side are used as boundaries to divide the basic component into a one-end-side area between the one-end-side-bottom-point line and the vertex line, and an other-end-side area between the vertex line and the other-end-side-bottom-point line, the section 1-1 and the other-end-side area in the basic component of the first tape have the same shape, and the section 2-1 and the one-end-side area in the basic component of the second tape have the same shape.

6. The tape set according to claim 5, wherein the first tape further includes a section 1-2 that continues from the tip edge of the section 1-1, and a section 1-3 that continues from the edge of the wavy part on the other end side,
the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction, and
the section 1-2, the section 1-3, the section 2-2, and section 2-3 each have side edges extending inward.

7. The tape set according to claim 6, wherein the section 1-2 and the section 2-2 have the same shape, and the section 1-3 and the section 2-3 have the same shape.

8. The tape set according to claim 7, wherein the side edges of the section 1-2 smoothly continue from the side edges of the section 1-1,
the side edges of the section 2-2 smoothly continue from the side edges of the section 2-1,
the side edges of the section 1-3 smoothly continue from the side edges of the other-end-side area of the basic component of the first tape, and
the side edges of the section 2-3 smoothly continue from the side edges of the one-end-side area of the basic component of the second tape.

9. The tape set according to claim 5, wherein the first tape further includes a section 1-2 that continues from the tip edge of the section 1-1, and a section 1-3 that continues from the edge of the wavy part on the other end side,
the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction,
the section 1-2 and the section 2-2 each have side edges extending inward,
the section 1-3 and the section 2-3 each have side edges extending outward,
the side edges of the section 1-2 and the section 2-3 are adjoined to each other, and
the side edges of the section 1-3 and the section 2-2 are adjoined to each other.

10. The tape set according to claim 9, wherein the section 1-2 and the section 2-2 have the same shape, and the section 1-3 and the section 2-3 have the same shape.

11. The tape set according to claim 10, wherein the side edges of the section 1-2 have the same gradient as that of the side edges of the one-end-side area of the basic component of the first tape,
the side edges of the section 1-3 have the same gradient as that of the side edges of the one-end-side area of the basic component of the first tape,
the side edges of the section 2-2 have the same gradient as that of the side edges of the other-end-side area of the basic component of the second tape, and
the side edges of the section 2-3 have the same gradient as that of the side edges of the other-end-side area of the basic component of the second tape.

12. The tape set according to claim 2, wherein the section 1-1 and the section 2-1 have the same shape.

13. The tape set according to claim 12, wherein the section 1-1 and the section 2-1 each have side edges extending outward.

14. The tape set according to claim 13, wherein when a one-end-side-bottom-point line extending in the width direction through bottom points on the one end side, a vertex line extending in the width direction through vertexes, and an other-end-side-bottom-point line extending in the width direction through bottom points on the other end side are used as boundaries to divide the basic component into a one-end-side area between the one-end-side-bottom-point line and the vertex line, and an other-end-side area between the vertex line and the other-end-side-bottom-point line, the section 1-1 and the other-end-side area in the basic component of the first tape have the same shape, and the section 2-1 and the one-end-side area in the basic component of the second tape have the same shape.

15. The tape set according to claim 14, wherein the first tape further includes a section 1-2 that continues from the tip edge of the section 1-1, and a section 1-3 that continues from the edge of the wavy part on the other end side, the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction, and the section 1-2, the section 1-3, the section 2-2, and the section 2-3 each have side edges extending inward.

16. The tape set according to claim 15, wherein the section 1-2 and the section 2-2 have the same shape, and the section 1-3 and the section 2-3 have the same shape.

17. The tape set according to claim 16, wherein the side edges of the section 1-2 smoothly continue from the side edges of the section 1-1, the side edges of the section 2-2 smoothly continue from the side edges of the section 2-1, the side edges of the section 1-3 smoothly continue from the side edges of the other-end-side area of the basic component of the first tape, and the side edges of the section 2-3 smoothly continue from the side edges of the one-end-side area of the basic component of the second tape.

18. The tape set according to claim 14, wherein the first tape further includes a section 1-2 that continues from the tip edge of the section 1-1, and a section 1-3 that continues from the edge of the wavy part on the other end side, the second tape further includes a section 2-2 that continues from the tip edge of the section 2-1 and whose tip edge is located along the same straight line as a tip edge of the section 1-3 extending in the width direction, and a section 2-3 that continues from the edge of the wavy part on the one end side and whose tip edge is located along the same straight line as a tip edge of the section 1-2 extending in the width direction, the section 1-2 and the section 2-2 each have side edges extending inward, the section 1-3 and the section 2-3 each have side edges extending outward, the side edges of the section 1-2 and the section 2-3 are adjoined to each other, and the side edges of the section 1-3 and the section 2-2 are adjoined to each other.

19. The tape set according to claim 18, wherein the section 1-2 and the section 2-2 have the same shape, and the section 1-3 and the section 2-3 have the same shape.

20. The tape set according to claim 19, wherein the side edges of the section 1-2 have the same gradient as that of the side edges of the one-end-side area of the basic component of the first tape, the side edges of the section 1-3 have the same gradient as that of the side edges of the one-end-side area of the basic component of the first tape, the side edges of the section 2-2 have the same gradient as that of the side edges of the other-end-side area of the basic component of the second tape, and the side edges of the section 2-3 have the same gradient as that of the side edges of the other-end-side area of the basic component of the second tape.

\* \* \* \* \*